United States Patent
Dinh et al.

(10) Patent No.: US 8,926,560 B2
(45) Date of Patent: Jan. 6, 2015

(54) DISTAL ACCESS BALLOON GUIDE CATHETER

(71) Applicant: Covidien LP, Mansfield, CT (US)

(72) Inventors: James Dinh, Irvine, CA (US); Maricruz Castenada, Mission Viejo, CA (US); Lynn Miyeko Shimada, Orange, CA (US); Seferino Enrique Torres, Santa Ana, CA (US); Brian Michael Strauss, Trabuco Canyon, CA (US); Jeffrey J. Valko, San Clemente, CA (US)

(73) Assignee: Covidien LP, Mansfield, MA (US)

( * ) Notice: Subject to any disclaimer, the term of this patent is extended or adjusted under 35 U.S.C. 154(b) by 149 days.

(21) Appl. No.: 13/623,941

(22) Filed: Sep. 21, 2012

(65) Prior Publication Data

US 2013/0253417 A1  Sep. 26, 2013

Related U.S. Application Data

(60) Provisional application No. 61/538,719, filed on Sep. 23, 2011.

(51) Int. Cl.
| | | |
|---|---|---|
| *A61M 25/00* | (2006.01) | |
| *A61M 25/01* | (2006.01) | |
| *A61M 25/10* | (2013.01) | |
| *A61M 25/06* | (2006.01) | |
| *A61B 19/00* | (2006.01) | |

(52) U.S. Cl.
CPC ....... *A61M 25/0053* (2013.01); *A61M 25/0012* (2013.01); *A61M 25/005* (2013.01); *A61M 25/0108* (2013.01); *A61M 25/1036* (2013.01); *A61M 2025/0059* (2013.01); *A61M 2025/0681* (2013.01); *A61B 2019/5466* (2013.01)
USPC ....... 604/103.09; 604/524; 604/526; 604/527

(58) Field of Classification Search
CPC ..................... A61M 25/0012; A61M 25/0043; A61M 25/005; A61M 25/0052; A61M 25/0053; A61M 25/1036; A61M 25/1025; A61M 25/0144; A61M 2025/0043; A61M 2025/0005; A61M 2025/0681; A61M 2025/1061; A61M 2025/1063
USPC ..................................... 604/103.09, 523–527
See application file for complete search history.

(56) References Cited

U.S. PATENT DOCUMENTS 4,676,229 A  *  6/1987  Krasnicki et al. ............. 600/140
5,358,493 A     10/1994  Schweich, Jr. et al.

(Continued)

FOREIGN PATENT DOCUMENTS

| EP | 1955724 | 8/2008 |
| JP | 11-262529 | 9/1999 |

(Continued)

OTHER PUBLICATIONS

International Search Report for PCT/US2012/045184, mailing date Apr. 10, 2012, 6 pages.

(Continued)

*Primary Examiner* — Quynh-Nhu H Vu
(74) *Attorney, Agent, or Firm* — Elizabeth A. O'Brien, Esq.

(57) ABSTRACT

Distal access balloon guide catheter system and methods for delivering implantable devices, catheters, or substances in or near and/or restoring flow through body lumens, such as blood vessel lumens, or inflating balloons affixed to the distal end of the guide catheter system are described. A Distal access balloon guide catheter having a proximal region, an optional medial region of intermediate flexibility, and distal region possessing high flexibility, high resistance to kinking and a large lumen to wall thickness ratio. The balloon is inflated by means of a kink-resistant secondary lumen embedded within the walls of the balloon guide catheter system tubing.

52 Claims, 7 Drawing Sheets

(56) References Cited

U.S. PATENT DOCUMENTS

| | | | |
|---|---|---|---|
| 5,380,304 A | 1/1995 | Parker | |
| 5,405,338 A | 4/1995 | Kranys | |
| 5,454,795 A | 10/1995 | Samson | |
| 5,456,665 A | 10/1995 | Postell et al. | |
| 5,538,512 A | 7/1996 | Zenzon et al. | |
| 5,573,520 A | 11/1996 | Schwartz et al. | |
| 5,658,264 A | 8/1997 | Samson | |
| 5,695,483 A | 12/1997 | Samson | |
| 5,700,253 A | 12/1997 | Parker | |
| 5,728,063 A * | 3/1998 | Preissman et al. | 604/103.09 |
| 5,795,341 A | 8/1998 | Samson | |
| 5,853,400 A | 12/1998 | Samson | |
| 5,876,386 A | 3/1999 | Samson | |
| 5,879,499 A | 3/1999 | Corvi | |
| 6,004,310 A | 12/1999 | Bardsley et al. | |
| 6,022,343 A | 2/2000 | Johnson et al. | |
| 6,036,670 A | 3/2000 | Wijeratne et al. | |
| 6,159,187 A | 12/2000 | Park et al. | |
| 6,171,295 B1 | 1/2001 | Garabedian et al. | |
| 6,193,705 B1 | 2/2001 | Mortier et al. | |
| 6,213,995 B1 | 4/2001 | Steen et al. | |
| 6,254,588 B1 | 7/2001 | Jones et al. | |
| 6,258,080 B1 | 7/2001 | Samson | |
| 6,358,238 B1 | 3/2002 | Sherry | |
| 6,368,315 B1 | 4/2002 | Gillis et al. | |
| 6,436,090 B1 | 8/2002 | Sanchez et al. | |
| 6,451,005 B1 | 9/2002 | Saitou et al. | |
| 6,485,457 B1 | 11/2002 | Hisamatsu et al. | |
| 6,503,223 B1 | 1/2003 | Sekido et al. | |
| 6,589,227 B2 | 7/2003 | Sønderskov Klint | |
| 6,616,651 B1 | 9/2003 | Stevens | |
| 6,702,802 B1 | 3/2004 | Hancock et al. | |
| 6,706,025 B2 | 3/2004 | Engelson et al. | |
| 6,808,520 B1 | 10/2004 | Fourkas et al. | |
| 6,991,626 B2 | 1/2006 | Wantink et al. | |
| 7,001,369 B2 | 2/2006 | Griffin et al. | |
| 7,540,865 B2 | 6/2009 | Griffin et al. | |
| 7,704,245 B2 | 4/2010 | Dittman et al. | |
| 7,794,448 B2 * | 9/2010 | Grandt et al. | 604/524 |
| 7,846,148 B2 | 12/2010 | Zhou | |
| 7,896,861 B2 | 3/2011 | McFerran et al. | |
| 8,298,210 B2 * | 10/2012 | Provost-Tine et al. | 604/527 |
| 2002/0123738 A1 | 9/2002 | Jansen et al. | |
| 2003/0028173 A1 * | 2/2003 | Forsberg | 604/527 |
| 2003/0135198 A1 | 7/2003 | Berhow et al. | |
| 2005/0043713 A1 | 2/2005 | Zhou | |
| 2005/0070879 A1 | 3/2005 | Coyle et al. | |
| 2005/0070881 A1 * | 3/2005 | Gribbons et al. | 604/525 |
| 2005/0234427 A1 * | 10/2005 | Eder | 604/526 |
| 2006/0020256 A1 | 1/2006 | Bell et al. | |
| 2006/0030835 A1 | 2/2006 | Sherman et al. | |
| 2006/0200074 A1 | 9/2006 | Zadno-Azizi | |
| 2006/0200110 A1 * | 9/2006 | Lentz et al. | 604/524 |
| 2006/0253102 A1 | 11/2006 | Nance et al. | |
| 2009/0166913 A1 | 7/2009 | Guo et al. | |
| 2011/0172643 A1 | 7/2011 | Jansen et al. | |

FOREIGN PATENT DOCUMENTS

| | | |
|---|---|---|
| JP | 2001-508670 | 7/2001 |
| JP | 2008-512196 | 4/2008 |
| WO | WO 97/44082 | 11/1997 |
| WO | WO 2006/031582 A2 | 3/2006 |
| WO | WO 2009/085486 | 7/2009 |

OTHER PUBLICATIONS

European Search Report for EP 12 18 5267, mailing date Feb. 28, 2013, 3 pages.

International Search Report for PCT/US2011/54600, mailing date Nov. 1, 2013, 3 pages.

The Written Opinion of the International Searching Authority for PCT/US2012/045184, 7 pages.

\* cited by examiner

DISTAL ACCESS BALLOON GUIDE CATHETER

CROSS REFERENCE TO RELATED APPLICATIONS

The present application claims the benefit of priority to U.S. Provisional Application Ser. No. 61/538,719, filed on Sep. 23, 2011, the entire contents of which are incorporated by reference.

BACKGROUND

1. Technical Field

The present disclosure relates generally to medical devices and methods and more particularly to catheter-based systems and methods usable for accessing, diagnosing, or treating defects in blood vessels, such as blood vessels of the brain.

2. Background of the Related Art

Stroke is a common cause of death and disability. In the United States, approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation (AVM), causing bleeding into the brain tissue and resultant infarction of brain tissue. The remaining 80% of strokes are due to ischemia that occurs due to occlusion of a blood vessel that deprives brain tissue of oxygen-carrying blood. Ischemic strokes are often caused by emboli or pieces of thrombotic tissue that have dislodged and traveled from other body sites, or from the cerebral vessels themselves, to occlude in the narrow cerebral arteries more distally. When a patient presents with neurological symptoms and signs, which resolve completely within 1 hour, the term transient ischemic attack (TIA) is used. Etiologically, TIA, and ischemic stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

To reach these lesions or occlusions microcatheter and microguidewire must be employed, but often the column support of these microcatheters is not strong enough to navigate through the distal reaches of the neurovasculature to effectively treat these sites. Often guide catheters are employed to act as a conduit to help support microcatheter access. Traditional guide catheters designed for coronary or peripheral use (U.S. Pat. No. 5,180,376 & U.S. Pat. No. 5,484,425 Fischell, U.S. Pat. No. 5,045,072 Castillo, U.S. Pat. No. 5,279,596 Castaneda, U.S. Pat. No. 5,454,795 Samson and U.S. Pat. No. 5,733,400 Gold), typically are not positioned above the skull base and limit their effectiveness in supporting microcatheters in the distal cerebrovasculature. Newer distal access guide catheters have been developed which are slightly longer, thinner, a bit more flexible than the early generations, but are constructed with the same manufacturing techniques as described in U.S. Pat. No. 5,180,376 & U.S. Pat. No. 5,484,425 Fischell, U.S. Pat. No. 5,045,072 Castillo, U.S. Pat. No. 5,279,596 Castaneda, U.S. Pat. No. 5,454,795 Samson and U.S. Pat. No. 5,733,400 Gold, but have not solved the kinking problem (e.g., Neuron Penumbra Recall—Oct. 2, 2009).

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the terms proximal and distal refer to a direction or a position along a longitudinal axis of a catheter or medical instrument. The term "proximal" refers to the end of the catheter or medical instrument closer to the operator, while the term "distal" refers to the end of the catheter or medical instrument closer to the patient. For example, a first point is proximal to a second point if it is closer to the operator end of the catheter or medical instrument than the second point. The measurement term "French", abbreviated Fr or F, is defined as three times the diameter of a device as measured in mm. Thus, a 3 mm diameter catheter is 9 French in diameter. The term "operator" refers to any medical professional (i.e., doctor, surgeon, nurse, or the like) performing a medical procedure involving the use of aspects of the present disclosure described herein.

The devices and methods described below provide a catheter device having a tubular member, an inner liner, a secondary balloon inflation/deflation channel, and an outer cover. The tubular member has an inner lumen and an outer surface. The tubular member has a metal helix having a helical gap and a polymeric material disposed within the helical gap. The inner liner extends through the lumen of the tubular member and defines an inner lumen of the catheter. The outer covering is disposed on the outer surface of the tubular member. The dimension(s) of the metal helix and/or the width of the helical gap may be constant over the entire length of the catheter or may be varied to provide for regionalized differences in flexural properties and/or kink resistance. The polymeric material disposed within the helical gap is different from the materials of the inner liner and outer cover. The components of the catheter device may be sized and constructed such that a distal region of the catheter device has an inner diameter to wall thickness ratio of from about 16:1 to about 24:1 (preferably about 16:1) and the following properties: a) a lateral flexibility of greater than 1,200 degree/in-lb and/or b) a kink radius of about 0.174 inch+/−0.008 inch or less and/or a tensile strength of 22N ultimate tensile strength (UTS).

The method for manufacturing a catheter includes the steps of: A) forming or obtaining a metal helix having a helical gap; B) fill the helical gap with polymeric material such that the polymeric material and the metal helix, in combination, form a tubular member having an outer surface and a lumen; C) positioning an inner liner within the lumen of the tubular member; D) creating a flattened polymeric side channel along the exterior of the inner liner and under the metal helix; and E) placing an outer cover on the outer surface of the tubular member. The polymeric material may be a cast polyurethane material, such as a polyurethane thermoset adhesive. Alternatively, the flattened polymeric side channel could be located outside the metal helix within the outer cover.

A method for treating or diagnosing a disorder in a human or animal subject includes the steps of A) inserting into the subject's vasculature a catheter device of the type described herein, B) inflating a balloon affixed proximate the distal end of the catheter device for the purpose of vessel occlusion, angioplasty, vessel remodeling, forming a temporary neck bridge, providing a form for embolic material fixation, stenting, flow diversion, and the like, and C) delivering a substance or device through the lumen of the catheter device and using the substance or device to treat or diagnose the disorder. The catheter device may be advanced into a blood vessel located within the subjects skull or which carry blood to or from the brain. Examples of blood vessels into which the catheter devices may be advanced include the carotid arteries, cerebral arteries, anterior cerebral artery, middle cerebral artery and posterior cerebral artery.

A system usable for performing a therapeutic or diagnostic task at a location within the body of a human or animal subject includes: a) distal access balloon catheter that has a proximal portion, a distal portion, a lumen and a distal end opening, the catheter distal tip being highly kink resistant, flexible, and with an inner diameter to catheter wall ratio of greater than 16 with a lateral stiffness (flexibility) of greater than 1,200 degrees/in-lb; and b) working devices that are advance-able though the lumen of the catheter and out of its distal opening, the working devices being useable to perform the therapeutic or diagnostic task. Examples of the types of working devices that may be used in this system include but are but are not limited to: i) devices for removing thrombus or other obstructive matter from body lumens and/or to the distal opening of the access aspiration guide catheter for aspiration; ii) flow restoration devices useable to facilitate flow of a fluid though or around an obstruction within a body lumen; iii) devices for deploying or delivering implants (e.g., implantable occlusion coils or implantable embolic devices); and/or iv) devices that temporarily occlude the lumen.

A method for performing a therapeutic or diagnostic task at a location within the body of a human or animal subject, includes the steps of: a) inserting into the subject's body a catheter that has a proximal portion, a distal portion, a main lumen extending therethrough, and a distal end opening, the catheter distal tip being highly kink resistant, flexible, and with a catheter inner diameter to catheter wall ratio of greater than 16 with a lateral stiffness (flexibility) of greater than 1,200 degrees/in-lb. The catheter further includes a secondary side lumen positioned parallel to the axis of the main lumen and has a polymeric tube embedded within a polymeric elastomeric surround, b) positioning the distal end opening of the catheter distally in a desired body lumen, c) inflating a balloon located near the distal end of the catheter with fluid injected through the side lumen, and d) advancing a working device though the main lumen of the catheter and out of its distal opening; and, using the working device to perform the therapeutic or diagnostic task. Examples of the types of working devices that may be used in this method include but are but are not limited to: i) devices for removing thrombus or other obstructive matter from body lumens and/or to the distal access aspiration guide catheter for aspiration; ii) flow restoration devices useable to facilitate flow of a fluid though or around an obstruction within a body lumen; and iii) devices for deploying or delivering implants (e.g., implantable occlusion coils or implantable embolic devices); and/or iv) devices that temporary occlude the lumen.

A method for removing obstructive matter from a body lumen, includes the steps of: a) distal access catheter that has a proximal portion, a distal portion, a main lumen extending therethrough and further including a distal end opening, a side lumen configured to facilitate fluid passage through the side lumen, a balloon affixed over and operably connected to the side lumen near the distal end of the catheter, the catheter distal tip being highly kink resistant, flexible, and with a inner diameter to catheter wall ratio of >16 and; b) positioning the catheter, such that its distal end opening is within a body lumen; c) inflating the balloon with fluid injected through the side lumen; d) moving obstructive matter through the distal end opening and into the lumen of the catheter; e) deflating the balloon by withdrawing fluid from the balloon interior using the side channel; and f) removing the catheter along with the obstructive matter that has been moved into the lumen of the catheter. Negative pressure may be applied through the lumen of the catheter to aspirate obstructive matter through the distal end opening and into the lumen of the catheter. Also, Step d of the method may include advancing an obstructive matter moving device (e.g., an embolectomy or thrombectomy device) from the catheter and using the obstructive matter-moving device to move obstructive matter through the distal end opening and into the lumen of the catheter. Step d can comprise injection of therapeutic fluids, solids, devices, or materials through the main lumen of the catheter.

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Figure 1:
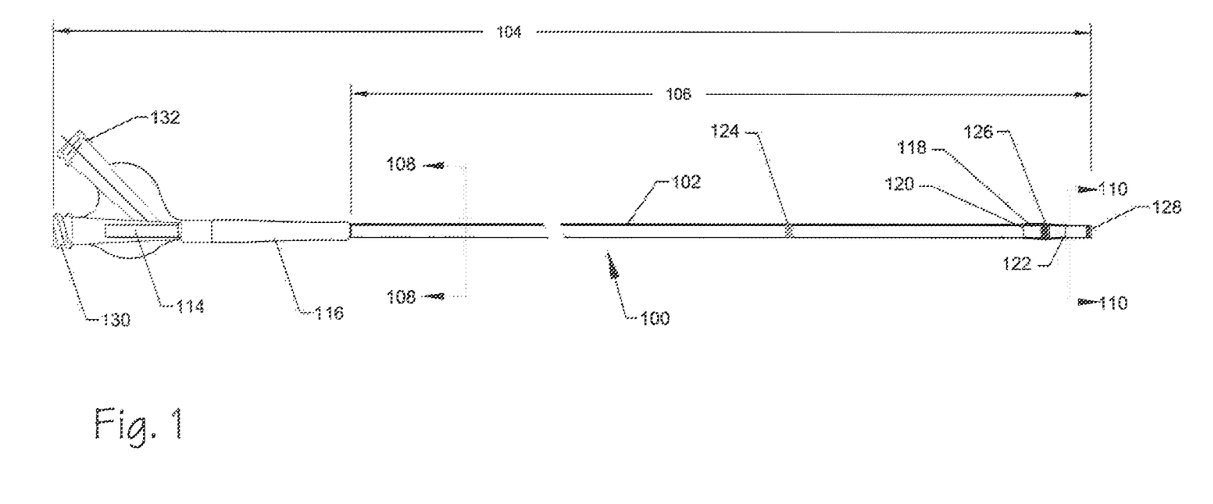
FIG. 1 illustrates a side view of a balloon catheter device having a hub region and two regions of tubing.
Figure 2A:
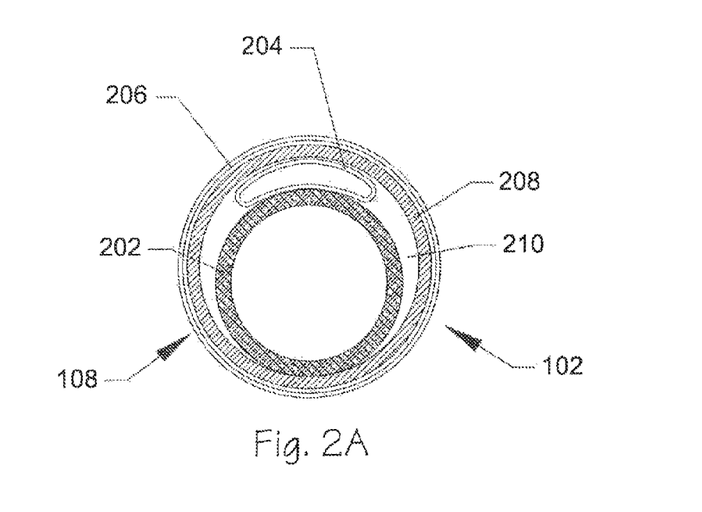
FIG. 2A illustrates a lateral cross-sectional view of a proximal region of catheter tubing having a main lumen and a balloon inflation lumen.
Figure 2B:
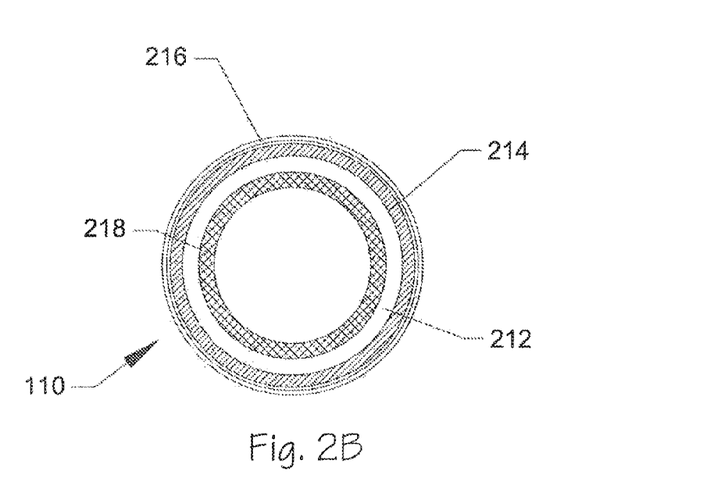
FIG. 2B illustrates a lateral cross-sectional view of a distal region of catheter tubing.

FIG. 1 illustrates a side view of a balloon catheter 100 further having a length of catheter tubing 102, a hub 114, a strain relief 116, and a balloon 118 further including a proximal bond 120 and a distal bond 122. The length of catheter tubing 102 further includes a distal radiopaque marker 128, a balloon radiopaque marker 126, and a transition zone 124. A proximal tubing cross-section 108-108 defines the point where the tubing of FIG. 2A has been laterally sectioned. A distal tubing cross-section 110-110 defines the point where FIG. 2B is defined. The catheter 100 includes an overall length 104 and a working, or effective, length 106.

Referring to FIG. 1, the guide catheter 100 is terminated, at its proximal end, with the hub 114, and can further include a Luer or hemostasis valve (not shown) operably connected to a port 130 which is operably connected to a central through lumen (not shown) of the guide catheter 100. The hub 114 can further include a connector offering at least one other access port 132, which can be valved or be terminated with a stopcock, Luer lock, bayonet mount, Luer slip fitting, etc.

The guide catheter tubing 102 can include a proximal region and a distal region. The distal region is more flexible than the proximal region. The distal region and the proximal region both maintain high column strength, torque resistance, and resistance to kinking. The catheter tubing 102 is configured with a very thin wall such that the size of the inner central lumen (not shown) is maximized for a given catheter tube 102 outside diameter. The guide catheter tubing 102 can include an intermediate region affixed at its distal end to the proximal end of the distal region and affixed at its proximal end to the distal end of the proximal region. The intermediate region can carry a side channel or the side channel can terminate prior to the intermediate region.

The proximal body segment is configured to exhibit sufficient column strength to permit axial positioning of the catheter through a patient's vasculature. The catheter body may further include other components, such as radiopaque fillers; colorants; reinforcing materials; reinforcement layers, such as braids and helical reinforcement elements; flexible adhesive potting, or the like. In particular, the proximal body segment may be reinforced in order to enhance its column strength and torqueability while preferably limiting its wall thickness and outside diameter.

The hub 114 is affixed to the proximal end of the catheter tube 102. The strain relief 116 is affixed, at its proximal end, to the hub 114. The two radiopaque (RO) marker bands 126, 128 are embedded, potted, adhesively bonded, welded, or otherwise affixed to the catheter tubing 102.

The hub 114 can be fabricated from a variety of polymers selected from materials including, but not limited to, polyethylene, polypropylene, acrylonitrile butadiene styrene (ABS), polysulfone, polycarbonate, polyvinyl chloride, polystyrene, polyester, and the like. The hub 114 can also be fabricated from metals such as, but not limited to, stainless steel, titanium, cobalt nickel alloy, and the like. The hub 114 comprises a through lumen (not shown) that can slidably accept devices up to the indicated size of the guide catheter subassembly 100, namely about 4, 5, 6, 7, 8, and 9 French, for example. The hub 114 can comprise a strain relief in the region where it is affixed to the tubing of the guide catheter subassembly 100 to minimize kinking and transfer forces to the guide catheter subassembly 100 under maximum control. Attachment between the hub 114 and other components of the subassembly 100 can comprise ultraviolet (UV) light curing adhesive such as, but not limited to, Dymax™ 1128-M-VT UV curing adhesive, or the like. The attachment between the hub 114 and the other components of the catheter subassembly 100 can also comprise cyanoacrylate adhesive such as, but not limited to, Loctite 4011, and the like.

The strain relief 116 comprises generally elastomeric materials and serves to support the tubing 102 and prevent kinking in the region where the rigid hub 114 is affixed to the tubing 102.

The catheter 100 disclosed herein may readily be adapted for use throughout the body wherever it may be desirable to introduce a very flexible thin walled catheter and kink resistant, which provides a relatively large diameter aspiration or supported working channel and a balloon disposed on a distal portion of the catheter tubing. For example, catheter shafts in may be dimensioned for use throughout the coronary and peripheral vasculature, the gastrointestinal tract, the urethra, ureters, Fallopian tubes and other lumens and potential lumens, as well. The lumen structure may also be used as a minimally invasive percutaneous tissue tract expander, such as for diagnostic or therapeutic access to a solid tissue target (e.g., breast biopsy or tissue excision). Although the catheter is termed a guide catheter herein, it may not be a guide catheter but rather a final catheter that is used for purposes other than guiding a secondary catheter therethrough. Further, the catheter may also have a rapid exchange configuration.

When present, the optional radiographic marker 128 will typically be provided at least at the distal end of the catheter 100. Other radiopaque markers 126 may be provided elsewhere, such as on the support coil, if it is not already radiopaque. A radiopaque marker 126, 128 that may be used includes a metal band, which is fully recessed within the distal end of the proximal body segment. Suitable marker bands 126, 128 can be produced from a variety of materials, including platinum, gold, and tungsten/rhenium alloy. The radiopaque metal band can be recessed in an annular channel formed at the distal end of the proximal body segment.

The radiopaque marker bands 126, 128 can be fabricated from platinum iridium wire having a diameter of about 0.002 inches. Materials comprised by the radiopaque markers 126, 128 can include platinum, platinum-iridium, gold, tantalum, barium sulfate, bismuth sulfate, and the like. The radiopaque markers 126, 128 can comprise or be configured as a coil of round wire, flat wire, or a wire with any other cross-section, or it can be configured as an axially elongate cylindrical band, as a serpentine band of wire, or the like. The radiopaque markers 126, 128 can comprise a length of about 0.5 mm to about 5 mm. The radiopaque markers 126, 128 can be embedded within the elastomeric adhesives and be disposed between the innermost layer 102, 220 and the outermost layer of polymer 206 and 216.

Diameters outside of the disclosed ranges may also be used, provided that the functional consequences of the diameter are acceptable for the intended purpose of the catheter. For example, the lower limit of the diameter for any portion of tubular body in a given application will be a function of the number of fluid or other functional lumen contained in the catheter, together with the acceptable minimum aspiration flow rate and collapse resistance.

The tubular catheter body 102 possesses sufficient structural integrity (e.g., column strength or "pushability") to permit the catheter to be advanced to distal locations without buckling or undesirable bending of the tubular body 102. The ability of the tubular catheter body 102 to transmit torque may also avoid kinking upon rotation, to assist in steering. The tubular catheter body 102, and particularly the distal section, may be provided with any of a variety of torque and/or column strength enhancing structures. For example, axially extending stiffening wires, spiral wrapped support layers, braid(s) or 10 woven reinforcement filaments may be built into or layered on all or part of the tubular catheter body.

The proximal section may not be required to traverse particularly low profile or tortuous arteries. For coronary vascular applications, for example, the proximal section will be mostly or entirely within a relatively large diameter guide catheter or it might reside within the aorta, vena cava or other large diameter vessel for a substantial portion of its length. The transition can be located on the catheter shaft to correspond approximately with the distal end of the guide catheter when the balloon and/or distal end is/are at the treatment site. For certain other applications, such as intracranial catheterizations, the distal section is preferably at least about 5 cm long and small enough in diameter to pass through vessels as small as 3 mm or 2 mm or smaller. Catheters 100 for this application may have a proximal section length of between about 60 cm to about 150 cm and a distal section length of between about 5 cm to about 15 cm, and the distal section is able to track a tortuous path of at least about 5 cm through vessels of less than about 3 mm lumen ID.

The number of catheter 100 tubular body sections may vary from one to five or more with a number of sections varying between two to four. A two body section catheter 100 is presented although an intermediate (third) body section is discussed throughout this disclosure. The intersections, interfaces, transitions, or other junctures between the proximal section, the distal section, and any sections located therebetween can include overlaps, partial overlaps, overlaps of reinforcing structures, rings of adhesives such as ultraviolet (UV) curing adhesives, and the like. The junctures can be complete or indistinct whereas one or more of an exterior outer jacket, an inner liner, a potting material, a reinforcing layer, a combination thereof, or the like, can terminate well into either the proximal or the distal section or one of the intermediate sections while.

FIG. 2A illustrates a lateral cross-section 108 of a proximal region of tubing in a catheter tube 102. The tube 102 comprises a proximal inner liner 202, a side channel defined by a length of tubing 204, a length of proximal coil reinforcement 208, an outer jacket of polymeric material 206, and a filling or potting of elastomeric adhesive 210 between the proximal inner liner 202 and the outer jacket 206.

Referring to FIG. 2A, the side channel 204 can be fabricated from materials such as, but not limited to, polyimide, polyamide, polyester, polyimide copolymers, and the like. The side channel 204 can be extruded in an approximately round cross-section and then be compressed into its curved elliptical shape. The side channel 204 can be extruded in the curved oval or elliptical cross-section shown in FIG. 2A. The side channel 204 can be assembled directly over the inner liner 202 or it can be separated from the inner liner 202 by a layer of polymer, elastomer, potting, metal or polymeric mesh, or the like. The overall cross-sectional shape is generally eccentric since the side channel 204 coexists with the inner liner 202 within the outer jacket 206.

FIG. 2B illustrates a lateral cross-section 110 of a distal tube in a two section catheter tube 102. The cross-section 110 of the catheter tube 102 includes the distal liner 218, an annular region of elastomeric adhesive potting 212 surrounding a distal spring temper coil 214, and an outer jacket 216.

Referring to FIG. 2B, the distal inner liner 218 can be an extension of the proximal inner liner 202 or it can be a different liner fabricated from different materials, diameters, thicknesses, etc. The distal liner 218 can be the same, continuous liner as the proximal liner 202. The distal inner liner 218 can be the same as the proximal inner liner 202, and is an extension thereof. The distal inner liner 218 can be integral to the proximal inner liner 202 but is thinned out in wall thickness. The distal inner liner 218 is prepared by assembling it over a removable mandrel (not shown) which is removed at some point following manufacturing and prior to packaging. The distal inner liner 218 can be the same as the proximal inner liner 202, it can be butted against, it can be integral to, or it can be overlapped with the proximal inner liner 202. The distal inner liner 218 is surrounded by the distal reinforcing coil 214 and then potted with elastomeric material 212. The entire structure is encased within the distal outer jacket 216 and compressed using pressure and heat to form the final structure. The distal reinforcing coil 214 can differ from the proximal coil 208 in thickness, strut width, strut cross-sectional shape, material, or other property. Since there is no side channel 204, the distal region is smaller in diameter than the proximal region at the cross-section 108. In some embodiments, the distal region at the cross-section 110 can be about 1 French smaller in diameter than the proximal region. The diameter of the distal region can range from about the same as to about 2 French smaller than the diameter of the proximal region.

The distal elastomeric material 212 can be the same as the elastomeric potting 210 used in the proximal region or it can be different material or a similar material with different hardness or other mechanical property. The elastomeric material 212 can comprise two layers, one of which is disposed inside the distal reinforcing coil 214 and another layer which is disposed outside the distal reinforcing coil 214.

The tubing subassembly 102 further includes at least one radiopaque marker band 128 and can comprise a transition ring of UV adhesive 124. The catheter tubing subassembly 102 further can comprise an overlap region 126 disposed at the transition between the proximal layer of adhesive 210 and the distal layer of adhesive 210. The tubing subassembly 102 can further comprise at least one outer layer of polymeric shrink wrap tubing (not shown) in the optional intermediate region (not shown).

Figure 3A:
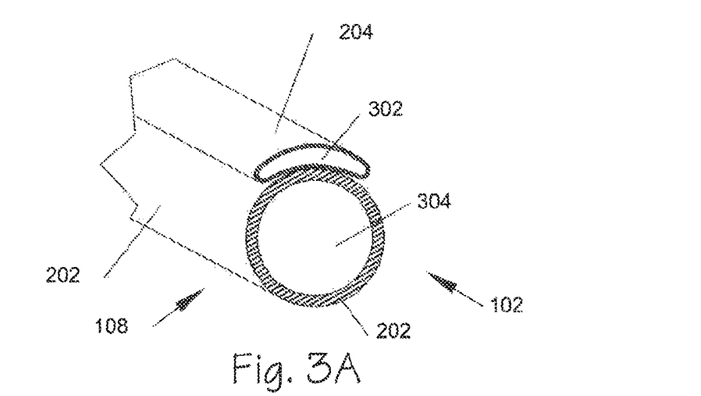
FIG. 3A illustrates an oblique view of a lateral cross-section of the proximal region of tubing subassembly including an inner liner, a central lumen, and a side lumen.

FIG. 3A illustrates an oblique view of a proximal catheter tubing initial subassembly 102 at cross-section 108 comprising the liner 202 further comprising a central lumen 304, the secondary tubing 204 further comprising a secondary lumen 302. This illustration describes the tubing subassembly 102 at an intermediate stage of manufacturing.

Referring to FIG. 3A, the inner liner 202 can comprise PTFE, PFA, FEP, or other lubricious polymer. The exterior diameter surface of the inner liner 202 can be etched to increase its roughness. Such etching can be performed using methodology including, but not limited to, plasma discharge treatment, mechanical abrasion, laser etching, and the like. The proximal inner liner 202 is generally disposed over a removable mandrel of the appropriate diameter, the mandrel (not shown) comprising a metallic core and an exterior lubricious coating such as PTFE, FEP, PFA, Parylene, or the like. This mandrel (not shown) is removed prior to the completion of manufacturing.

Figure 3B:
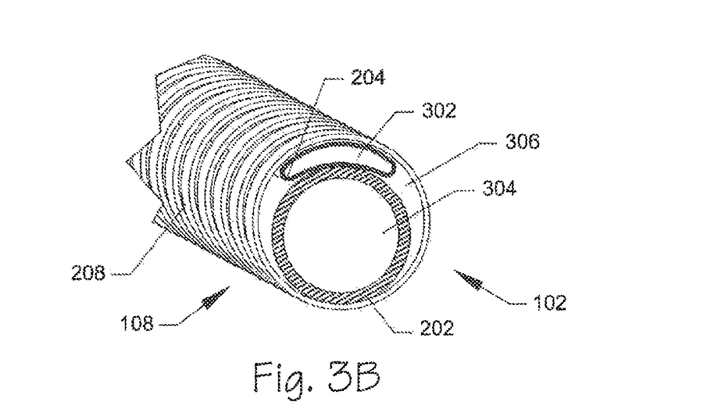
FIG. 3B illustrates an oblique, lateral cross-section of the proximal region of tubing with the inner liner and the side lumen covered by a metal coil reinforcement.

FIG. 3B illustrates an oblique view of a proximal catheter tubing secondary subassembly 102 at cross-section 108 comprising the proximal liner 202 further comprising the central lumen 304, the secondary tubing 204 further comprising the secondary lumen 302, a reinforcing coil 208, and an annulus 306 between the coil 208 and the liner 202. FIG. 3B illustrates the tubing subassembly 102 at a later intermediate stage of manufacture than that illustrated in FIG. 3A.

Referring to FIG. 3B, the annulus 306 surrounds the side channel 204 tubing. The annulus 306 can be filled with potting, elastomer, adhesive, polymer, or other material at this point in manufacturing or it can be empty for later injection of material therein.

Figure 4A:
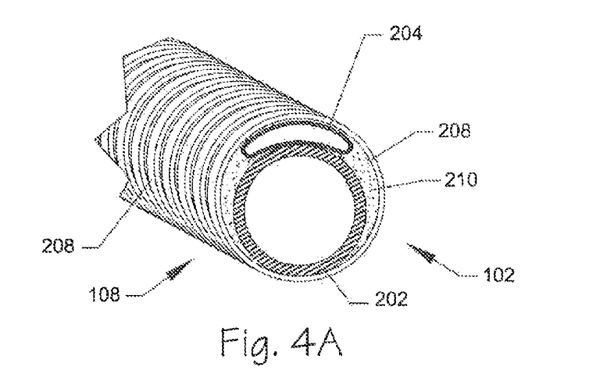
FIG. 4A illustrates an oblique view of a lateral cross-section of the proximal region of tubing subassembly with adhesive material potted in the space between the coil and the inner liner, further surrounding the side lumen.

FIG. 4A illustrates an oblique view of a proximal catheter tubing subassembly 102 at cross-section 108 comprising the proximal liner 202, the secondary tubing or side channel 204, the proximal reinforcing coil 208, and a region of potting 210 between the proximal coil 208 and the proximal liner 202.

Referring to FIG. 4A, the proximal inner liner 202 has been applied over the mandrel (not shown). The side channel 204 has been flattened and placed against the inner liner 202. The proximal coil 208 has been wrapped around the proximal inner liner 202 and the side channel 204. A first layer of potting 210 has been applied to the annulus 306 from FIG. 3B, between the proximal coil 208 and the proximal inner liner 202, as well as around the side channel 204. The potting 210 also extends slightly between the loops of the coil 208. The potting 210 may also be applied by an extrusion process, dip coated, spray coated, vapor deposition, or the like.

The first layer of potting 210 can comprise materials such as, but not limited to, silicone elastomer, isoprene, polyurethane elastomer, thermoplastic elastomers, adhesive elastomeric materials that are marketed under the trade name Flexobond™, supplied by Bacon Co., Irvine, Calif., and the like. Potting 210 may also be a polymer that is firmed up by solvent evaporation, cross linking, a room-temperature vulcanized (RTV) polymer, or the like.

Figure 4B:
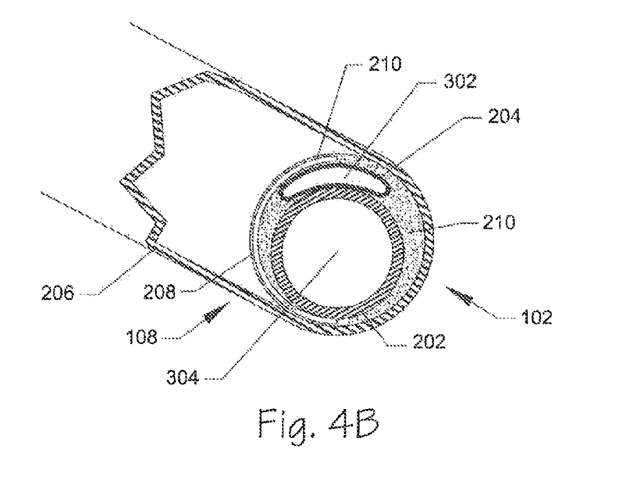
FIG. 4B illustrates an oblique view of a lateral cross-section of the proximal region of tubing subassembly with adhesive material potted around the exterior of the coil and between the coil elements further covered by an external wrapping.

FIG. 4B illustrates the proximal catheter tubing 102 subassembly at cross-section 108, comprising the proximal inner liner 202 further comprising the central lumen 304, the side channel 204 further comprising the side lumen 302, the reinforcing coil 208, the potting 210 around the proximal reinforcing coil 208, and further comprising a quantity of potting 210 between the proximal reinforcing coil 208 and the proximal outer jacket 206

Referring to FIGS. 4A and 4B, the potting, or adhesive layer 210, is disposed between the proximal outer jacket 206 and the proximal inner liner 202 and around the side channel 204 over the proximal regions of the subassembly 700, comprises materials such as, but not limited to, Flexobond 431™. The potting 210 can be the same as that applied in FIG. 4A or it can comprise materials that have different mechanical, thermal, or electrical properties.

Figure 5A:
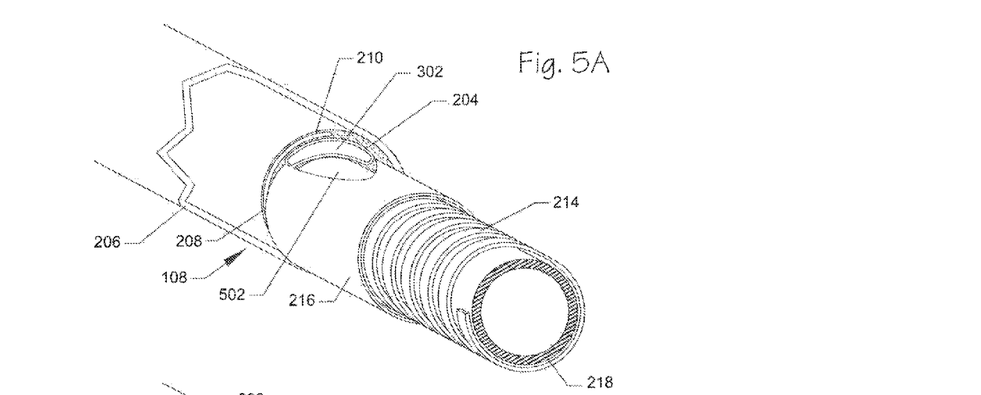
FIG. 5A illustrates an oblique view of a lateral section of the distal region of a catheter tubing subassembly showing a balloon inflation lumen, a skive to permit the balloon inflation lumen to communicate with a balloon, and a distal coil winding.

FIG. 5A illustrates an oblique view of a lateral cross-section of the catheter tubing 102 in the distal region. The distal catheter tubing 102 comprises the inner liner 218, the distal reinforcing coil 214, the region of potting 212 surrounding the distal coil 214, a skive or window 502, and a distal outer jacket 216.

Figure 5B:
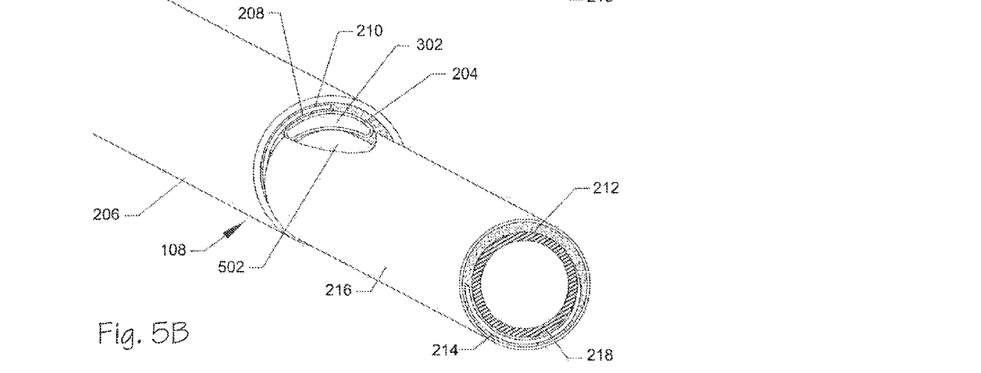
FIG. 5B illustrates an oblique view of the section illustrated in FIG. 5A further incorporating a potting of elastomeric material around the distal coil winding and surrounded by an outer jacket.

Referring to FIGS. 5A and 5B, the distal end of the catheter tubing at cross-section 110 is smaller in diameter than that of the proximal region cross-section 108. The side channel 204 no longer extends into the distal region and is terminated at a point where the side channel lumen 302 exits under a balloon (not shown). The skive or window 502 can optionally be provided to allow for fluid communication between the side channel lumen 302 to the interior volume of the balloon (not shown) since the end of the side channel lumen 302 may reside within or below the distal jacket 216. In some embodiments, the side channel lumen 302 terminates above the outer jacket 216 of the distal region and the skive or window 502 is not required. The side channel lumen emerges above the exterior of the outer jacket 216.

In an 8 French catheter 100, the wall thickness can range from about 0.0045 to 0.0055 inches, with a wall thickness of about 0.005 inches and the inside diameter of the catheter tubing 102 can preferably range from about 0.094 inches to about 0.096 inches.

In a 7 French catheter 100, the wall thickness can range from about 0.004 to 0.005 inches, with a wall thickness of about 0.0045 inches and the inside diameter of the catheter tubing 102 can preferably range from about 0.082 inches to about 0.084 inches.

In a 6 French catheter 100, the wall thickness can range from about 0.003 to 0.004 inches, with a wall thickness of about 0.0035 inches and the inside diameter of the catheter tubing 102 can preferably range from about 0.072 inches to about 0.073 inches.

In a 5 French catheter 100, the wall thickness can range from about 0.003 to 0.0035 inches, with a wall thickness of about 0.00325 inches and the inside diameter of the catheter tubing 102 can preferably range from about 0.059 inches to about 0.060 inches.

In a 4 French catheter 100, the wall thickness can range from about 0.0025 to 0.003 inches, with a wall thickness of about 0.00275 inches and the inside diameter of the catheter tubing 102 can preferably range from about 0.046 inches to about 0.047 inches.

The spacing on the distal coil 214 can be approximately 0.008, with a range of about 0.006 to 0.010 inches. The spacing on the medial coil (not shown) can be approximately 0.004 inches with a range of about 0.002 to 0.006 inches. The spacing on the proximal coil 208 can be approximately 0.001 inches with a range of about 0.0005 to 0.002 inches. The tighter the spacing of the coils 208, 214 the stiffer the system and the greater the torque carrying capability of the system. Thus, the proximal coil 208 is stiffer than a medial coil (not shown), which is, in turn, stiffer than the distal coil 214. The coils 208, 214 can be fabricated from nitinol with superelastic or pseudoelastic properties and preferably in a flat wire shape, although a round wire or a wire having any cross-sectional profile can also be used under certain circumstances. The coil wire 208, 214 can range in width from about 0.001 inches to about 0.010 inches and the thickness of the coil wire can range from about 0.0005 to about 0.005 inches. The coil wire 208, 214 preferably has spring characteristics and is not malleable. The coil wire 208, 214 can be fabricated from nitinol, as previously stated, but it can also be fabricated from materials such as, but not limited to, cobalt nickel alloy, titanium, stainless steel, polyester, polyethylene naphthalate (PEN), and the like.

The distal coil wire 214 can be wound around the distal inner liner 216 more tightly than the proximal coil wire 208 is wound around the proximal inner liner 202. This increased tightness of coil 214 wrapping facilitates a smaller diameter distal tubing 102 region relative to the proximal tubing 102 region. Furthermore, the spacing between the coils 214 in the distal region can be more open than the coils 208 in the proximal region. In the proximal coils 208, the gap between the coil windings 208 can range from about 0 to about 0.004 inches with a gap range of about 0.001 to 0.002 inches. The distal coils 214 can comprise a gap between windings that ranges from about 0.002 to about 0.012 inches with a range of about 0.004 to 0.008 inches.

The coils 208 and 214 can be wound exterior to the inner liner 202 and interior to the side channel 204, in addition to being wound exterior to the side channel.

The coils described herein may be composed of wires that have a flat-wire cross-section, a circular cross-section, or any other polygonal cross-section. Alternatively, in other embodiments, coils 208 and 214 may be formed from a metallic tube that is laser cut, chemically etched, or grinded to form a desired pattern. In another embodiment, coils 208 and 214 may be built upon a removable substrate by electrodeposition, vapor deposition, sintering, or any other processes that may be used to build coils 208 and 214 on a removable substrate. Further, the pitch of the coil windings, the inner diameter of the coil, and the outer diameter of the coil may vary along its length, In an alternative embodiment, a proximal braid and distal braid may be used instead of coils 208 and 214, respectively. The braids may be by winding one or more wires to form a helical coil or a braid. The wires may have a flat-wire cross-section, a circular cross-section, or any other polygonal cross-section. Alternatively, in other embodiments, the braids may be formed from a metallic tube that is laser cut, chemically etched, or grinded to form a desired pattern for me the braids. In another embodiment, the braids may be built upon a removable substrate by electrodeposition, vapor deposition, sintering, or any other processes that may be used to build the braids on a removable substrate. The pics per inch (PPI) for the braids may vary along the longitudinal length of the catheter to increase the flexibility of the catheter toward the distal end.

The tubing subassembly 102 construction for a catheter 100 having a working length 106 (catheter length exclusive of the hub 114, strain relief 116 or any other attachments) of 105-cm is as follows: The overall length 104 can be about 113-cm, the working or usable length 106 can be about 105-cm, the liner 202 length can be about 110-cm, the proximal coil 208 length can be about 96-cm, the medial coil length (not shown) can be about 6-cm, and the distal coil 214 length can be about 8-cm.

The liner 202 and coil 208 subassembly construction for a catheter 100 having a working length 106 of 115-cm is as follows: The overall length 104 can be about 123-cm, the working or usable length 106 can be about 115-cm, the liner 202 length can be about 120-cm, the proximal coil 208 length can be about 106-cm, the medial coil (not shown) length can be about 6-cm, and the distal coil 214 length can be about 8-cm.

The distal potting layer 212, disposed over the distal regions of the tubing subassembly 102, comprises materials such as, but not limited to, Flexobond 430™, supplied by Bacon Co., Irvine, Calif. The proximal first adhesive layer 210 can be configured to provide increased stiffness relative to that of the distal first potting layer 212. The distal adhesive or potting layer 212 generally is applied to the subassembly along the entire length of the tubing 102 and the thickness of the layers 210, 212 is approximately equal to, or slightly greater than that of the coil windings 208, 214.

The proximal second layer of adhesive can have a length of about 91-cm (range about 80-cm to about 100-cm) for a catheter having a 105-cm working length and about 101-cm (range about 90-cm to about 110-cm) for a catheter having a 115-cm working length. The length of the intermediate second layer of elastomeric adhesive can be about 5.5-cm with a range of about 3-cm to about 7-cm. The length of the distal layer of elastomeric adhesive can range between about 15-cm and 25-cm with an exemplary value of about 19.5-cm for catheters having working lengths of about 105-cm to about 115-cm. The overlap region around 124 or 126 can have a length of about 0.5-cm with a range of about 0.1-cm to about 1.0-cm. The length of the UV curable adhesive ring 124 can range from about 0.5-mm to about 2-mm with an exemplary value of about 1.0-mm.

The outermost layers of polymer 206, 216 can be fabricated from materials such as, but not limited to, polyester (PET), polyimide, Pebax™, polyamide, or the like. In some embodiments, the outermost layers of polymer 206 in the proximal region can be configured as heat shrink tubing having a thickness of about 0.00025 to about 0.002 inches with a range of about 0.005 to about 0.0015 inches. The outermost layer of polymer 216 in the distal region can comprise polyimide (Pebax™) heat shrink tubing having a thickness of between about 0.0005 and 0.002 inches. The distal outer polymer layer 216 can be sourced from Iridium Corporation. An optional intermediate outer layer of polymer (not shown} can comprise polyester (PET} having a wall thickness of about 0.00025 inches, with a range of about 0.0001 to about 0.001 inches. The outer polymer layers, being heat shrink wrap material, can be slidably placed over the catheter tubing subassembly 102 and heat shrunk down tightly over the second layers of adhesive and any other tubing components. The heat shrinking can be performed using a hot box or with a horizontal or vertical shrinking machine that automatically moves a ring or C-shaped heating element along the length of the catheter tubing to generate a smooth, constant diameter outer configuration.

The second layer of adhesive in the proximal region 210 preferably comprises Flexobond 431 but can also comprise other similar materials, such as but not limited to other 2-part urethane adhesives, 1-part urethane adhesive, or the like. The second layer of adhesive in the intermediate region (not shown) preferably comprises Flexobond 430 but can also comprise other similar materials, such as but not limited to other 2-part urethane adhesives, 1-part urethane adhesive, or the like. The second layer of adhesive 212 in the distal region preferably comprises Flexobond 430 soft mix but other similar materials can also be used.

A key element of the material selection is the resistance to degradation by certain solvents. The embodiments cited herein are resistant to attack by the solvent dimethyl sulfoxide (DMSO). DMSO is sometimes used as a carrier for embolic agents used in the brain to occlude arteriovenous malformations (AVM) for filling cerebrovascular aneurysms and compatibility with DMSO is extremely important for a cerebrovascular guide or aspiration catheter. The adhesives, potting materials, and aspiration guide catheter components including liners, adhesive layers, outer polymer layers, coils, braids, etc. are all resistant to any substantial chemical changes when brought into contact, even prolonged contact, with DMSO.

The balloon 118, can comprise a compliant balloon formed of material such as latex, silicone, polyurethane, C-Flex™ thermoplastic elastomer, Chronoprene™, Santoprene™ or the like, may be positioned at or near the distal end of the elongate catheter body 102. Such balloons 118 can be useful for occluding flow through the blood vessel in which the catheter is positioned when such flow occlusion is desired. In other embodiments, the balloon 118 can comprise substantially inelastic materials such as, but not limited to, polyester (PET), polyimide, polyamide, cross-linked polymers, and the like.

Following construction of the final catheter subassembly 100, any manufacturing mandrels (not shown) are removed. An obturator (not shown) can be inserted into the catheter subassembly 100 to maintain crush resistance during packaging, shipping and storage. The obturator can be used for packaging and shipping or it can be used as part of the aspiration guide catheter to track the aspiration guide catheter over a guidewire, etc. Thus, any obturator can beneficially comprise a central through lumen having a diameter capable of slidably accepting an approximate 0.010 inch diameter guidewire up to about a 0.018 inch diameter guidewire.

The proximal section of tubing 102 can retain radial strength but provide lateral flexibility. Additionally, that section desirably has a lateral flexibility (Stiffness}, such as would be measured by, for example, a Tinius-Olsen™ Stiffness Tester, of at least 1,200 degrees of deflection/inch-pound (measured at 20 degrees to 30 degrees of deflection, with a 0.005 lb load, over a 0.25" span), preferably 2,500 degrees of deflection/inch-pound. The radial compression strength of the section is quite high as compared to other distal sections found on comparable catheter distal sections of prior art guide catheters.

Access for the catheter 100 can be achieved using conventional techniques through an incision on a peripheral artery, such as right femoral artery, left femoral artery, right radial artery, left radial artery, right brachial artery, left brachial artery, right axillary artery, left axillary artery, right subclavian artery, or left subclavian artery. An incision can also be made on right carotid artery or left carotid artery in emergency situations.

The construction disclosed herein is suitable for guide catheter, catheter introducer, or balloon catheter as a stand-alone device. This construction results in a highly flexible device having high column strength, torqueability, superior kink-resistance unachievable in prior art devices having a thin wall tube of this size, and high tensile strength. The adhesive potting surrounding the coils 208, 214 and the side channel 204 maintain the side lumen 302 open or patent even when the catheter tubing 102 is bent around severely small radii. The inner lumen 304 is likewise protected against kinking or collapse by the reinforcing coils 208, 214 and the packing effects of the potting 210, 212.

Figure 6A:
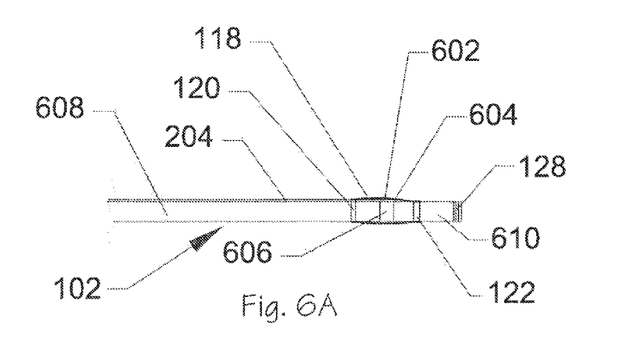
FIG. 6A illustrates a side view of the distal end of a catheter tube including a collapsed balloon.

FIG. 6A illustrates a side view of the catheter tube 102 comprising the uninflated balloon 118, the proximal balloon bond 120, the distal balloon bond 122, an interior balloon region of space 604 inside the balloon 118, the side channel lumen 204, a side channel lumen exit port 602, a tubing transition zone 606, a proximal tubing region 608, a distal tubing region 610, and the distal radiopaque marker 128.

Figure 6B:
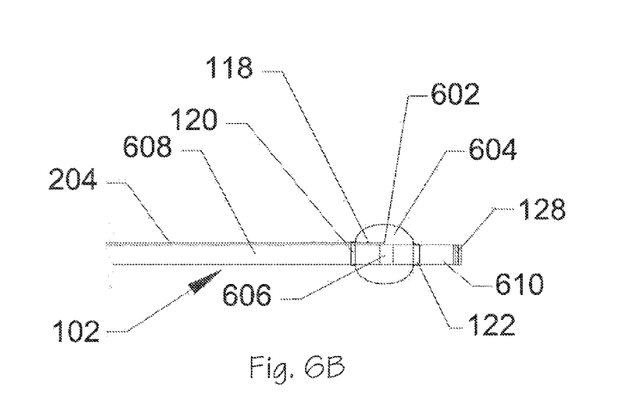
FIG. 6B illustrates a side view of the distal end of a catheter tube including an inflated balloon.

FIG. 6A illustrates a side view of the catheter tube 102 comprising the inflated balloon 118, the proximal balloon bond 120, the distal balloon bond 122, an interior balloon region of space 604 inside the balloon 118, the side channel lumen 204, a side channel lumen exit port 602, a tubing transition zone 606, a proximal tubing region 608, a distal tubing region 610, and the distal radiopaque marker 128.

The fabrication of the catheter 100 can comprise stretching the inner liner to size and positioning a PTFE inner liner 202 along the entire length of the desired catheter over a PTFE coated metal mandrel having very tight tolerances with regard to concentricity and diameter. The PTFE inner liner 202 is beneficially etched using plasma discharge or other treatment to created microscopic roughness in the outer wall of the inner liner. A section of polyimide side channel tubing 204 is flattened using a rolling mill and is then annealed at about 180° F. for about 2 hours. Platinum iridium or platinum wires 128 are wound into a coil around the distal end as well as in a proposed balloon area and are then bonded in place to the inner liner 202 using cyanoacrylate adhesive. Two nitinol coils having different characteristics, a proximal coil 210 and a distal coil 214, are laser welded together at the transition point where the two coils are affixed to each other. The welded coils 210, 214 are positioned over the flattened polyimide tubing and the PTFE liner. The proximal segment of the welded coil assembly is potted with Flexobond 431. The distal segment of welded coil assembly is potted with Flexobond 430. An outer layer of PET is heat shrunk over the coils, the polyimide side channel, the PTFE inner liner 202, and the potted Flexobond material along the entire proximal length of the catheter tubing 102. Palladium™ Pebax™ tubing is heat shrunk over the coil assembly, flat polyimide, PTFE, and Flexobond along the entire distal length of the catheter tubing 102. Pebax™ 250 tubing is heat fused at both ends of a pre-cut length of elastomeric balloon tubing (e.g. Chronoprene™). The hub (Y-connector) 114 is bonded to the proximal end of the tubing 102 using UV curable adhesive. The strain relief 116 is affixed to the hub 114 using cyanoacrylate or UV curable adhesive. The exit of the side channel lumen 302 is located generally central underneath the balloon tubing. The side channel lumen 302 is preferably configured to exit or terminate above the level of the exterior of the distal portion of the catheter tubing 102. Should the side channel lumen 302 terminate partially or completely beneath the outer surface of the distal tubing 102, it is beneficial to skive a port, fenestration, or window 502 in the tubing covering the exit to the side channel lumen 302 to allow the side channel lumen 302 to operably connect with the region exterior to the catheter tubing 102 and beneath the balloon 118.

Figure 7:
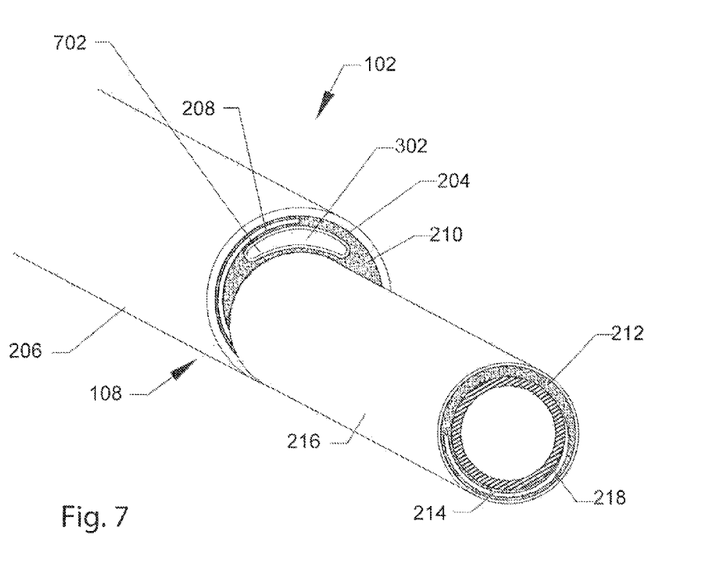
FIG. 7 illustrates an oblique view of the transition between a proximal segment and a distal segment of a length of balloon catheter tubing illustrating emergence of a side channel lumen outside the exterior of the distal segment.

FIG. 7 illustrates the transition 108 in a catheter tube 102 comprising the proximal jacket or outer layer 206, the distal jacket or outer layer 216, the proximal coil 208, the distal coil 214, the distal liner 218, the proximal liner 202 (not shown), the side channel 204, the side channel lumen 302, the proximal potting 210, the distal potting 212, and the exit 702 to the side channel lumen 302.

Referring to FIG. 7, the exit or termination 702 is located radially exterior to the distal jacket 216. The proximal potting 210 and the proximal coil 208 are visible at the termination of the proximal side channel 204 but in some embodiments, the proximal coil 208 is terminated prior to the termination 702. In the embodiments illustrated in FIG. 7, there is no need for windows in the distal jacket 216. The distal liner 218 is preferably an extension of, and the same as, the proximal liner 202 (not shown). The distal coil 214 can be wrapped more tightly around the distal liner 218 than is the proximal coil 208 wrapped around the proximal liner 202 to facilitate exposure of the exit 702. The outer jacket 216 can also be wrapped more tightly with less distal potting 212 than is the proximal outer jacket 206 wrapped resulting in a thicker mass of proximal potting 210. The asymmetry (non-concentricity) of the proximal outer jacket 206 and the distal outer jacket 216 can be accommodated by flexibility in the balloon (not shown) since the balloon 118 straddles the exit 702 and the distal balloon bond 122 is affixed to the outside of the outer distal jacket 216 while the proximal balloon bond 120 is affixed to the outside of the proximal outer jacket 206. The interior 604 of the balloon 118 is operably connected to the exit 702, which is operably connected to the side channel lumen 302.

The catheter device may be sized and constructed such that a distal region of the catheter device has an inner diameter to wall thickness ratio of from about 16:1 to about 24:1 (preferably about 16:1) and the following properties: a) a lateral flexibility of greater than 1,200 degree/in-lb and/or b) a kink radius of about 0.174 inch+/−0.008 inch or less and/or a tensile strength of 22N ultimate tensile strength (UTS).

The devices described above are intended for use in a method for manufacturing a catheter includes the steps of: A) forming or obtaining a metal helix having a helical gap; B) fill the helical gap with polymeric material such that the polymeric material and the metal helix, in combination, form a tubular member having an outer surface and a lumen; C) positioning an inner liner within the lumen of the tubular member; D) creating a flattened polymeric side channel along the exterior of the inner liner and under the metal helix; and E) placing an outer cover on the outer surface of the tubular member. The polymeric material may be a cast polyurethane material, such as a polyurethane thermoset adhesive.

The devices described above are intended for use in a method for treating or diagnosing a disorder in a human or animal subject includes the steps of A) inserting into the subject's vasculature a catheter device of the type described herein, B) inflating a balloon affixed proximate the distal end of the catheter device for the purpose of vessel occlusion, angioplasty, vessel remodeling, forming a temporary neck bridge, providing a form for embolic material fixation, stenting, flow diversion, and the like, and C) delivering a substance or device through the lumen of the catheter device and using the substance or device to treat or diagnose the disorder. The catheter device may be advanced into a blood vessel located within the subject's skull or which carry blood to or from the brain. Examples of blood vessels into which the catheter devices may be advanced include the carotid arteries, cerebral arteries, anterior cerebral artery, middle cerebral artery and posterior cerebral artery.

The devices described above are intended for use in a system for performing a therapeutic or diagnostic task at a location within the body of a human or animal subject. The devices include: a) distal access balloon catheter that has a proximal portion, a distal portion, a lumen and a distal end opening, the catheter distal tip being highly kink resistant, flexible, and with an inner diameter to catheter wall ratio of greater than 16 with a lateral stiffness (flexibility) of greater than 1,200 degrees/in-lb.; and b) working devices that are advance-able though the lumen of the catheter and out of its distal opening, the working devices being useable to perform the therapeutic or diagnostic task. Examples of the types of working devices that may be used in this system include but are but are not limited to: i) devices for removing thrombus or other obstructive matter from body lumens and/or to the distal opening of the access aspiration guide catheter for aspiration; ii) flow restoration devices useable to facilitate flow of a fluid though or around an obstruction within a body lumen; and iii) devices for deploying or delivering implants (e.g., implantable occlusion coils or implantable embolic devices) and/or iv) devices that temporarily occlude the lumen.

The devices described above are intended for use in a method for performing a therapeutic or diagnostic task at a location within the body of a human or animal subject, includes the steps of: a) inserting into the subject's body a catheter that has a proximal portion, a distal portion, a main lumen extending therethrough, a distal end opening, the catheter distal tip being highly kink resistant, flexible, with a catheter inner diameter to catheter wall ratio of greater than 16 with a lateral stiffness (flexibility) of greater than 1,200 degrees/in-lb, a secondary side lumen positioned parallel to the axis of the main lumen, and a polymeric tube embedded within a polymeric elastomeric surround; b) positioning the distal end opening of the catheter distally in a desired body lumen; c) inflating a balloon located near the distal end of the catheter with fluid injected through the side lumen; and d) advancing a working device though the main lumen of the catheter and out of its distal opening; and e) using the working device to perform the therapeutic or diagnostic task. Examples of the types of working devices that may be used in this method include but are but are not limited to: i) devices for removing thrombus or other obstructive matter from body lumens and/or to the distal access aspiration guide catheter for aspiration; ii) flow restoration devices useable to facilitate flow of a fluid though or around an obstruction within a body lumen; and iii) devices for deploying or delivering implants (e.g., implantable occlusion coils or implantable embolic devices) and/or iv) devices that temporary occlude the lumen.

The devices described above are intended for use in a method for removing obstructive matter from a body lumen, includes the steps of: a) distal access catheter that has a proximal portion, a distal portion, a main lumen extending therethrough and further including a distal end opening, a side lumen configured to facilitate fluid passage through the side lumen, a balloon affixed over and operably connected to the side lumen near the distal end of the catheter, the catheter distal tip being highly kink resistant, flexible, and with a inner diameter to catheter wall ratio of >16 and; b) positioning the catheter, such that its distal end opening is within a body lumen; c) inflating the balloon with fluid injected through the side lumen; d) moving obstructive matter through the distal end opening and into the lumen of the catheter; e) deflating the balloon by withdrawing fluid from the balloon interior using the side channel; and f) removing the catheter along with the obstructive matter that has been moved into the lumen of the catheter. Negative pressure may be applied through the lumen of the catheter to aspirate obstructive matter through the distal end opening and into the lumen of the catheter. Also, Step d) of the method may include advancing an obstructive matter moving device (e.g., an embolectomy or thrombectomy device) from the catheter and using the obstructive matter-moving device to move obstructive matter through the distal end opening and into the lumen of the catheter. Step d) can comprise injection of therapeutic fluids, solids, devices, or materials through the main lumen of the catheter.

It is to be appreciated that the disclosure has been described hereabove with reference to certain examples or embodiments of the disclosure but that various additions, deletions, alterations and modifications may be made to those examples and embodiments without departing from the intended spirit and scope of the disclosure. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

While the embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A catheter device comprising:
   an axially elongate tubular member comprising an inner lumen, an outer surface, a proximal end, and a distal end, the tubular member comprising a metal helix having a helical gap, and a polymeric potting material disposed within the helical gap;
   an inner liner extending through the lumen of the tubular member and defining an inner lumen of the catheter;
   an outer cover on the outer surface of the tubular member; and
   a balloon inflation channel disposed between the metal helix and the inner liner,
   wherein the polymeric potting material disposed within the helical gap is different from the materials of the inner liner and outer cover.

2. The catheter device of claim 1, wherein the metal helix comprises nickel titanium alloy.

3. The catheter device of claim 1, wherein the metal helix comprises flat wire or ribbon.

4. The catheter device of claim 3, wherein the flat wire or ribbon comprises Nitinol Type 1 having a width from about 0.003 inch through about 0.0125 inch and a thickness from about 0.001 inch through about 0.005 inch.

5. The catheter device of claim 1, wherein the helical gap has a non-continuous width.

6. The catheter device of claim 1, wherein the dimension(s) of the metal helix and/or width of the helical gap varies.

7. The catheter device of claim 1, wherein the helical gap has a width ranging from about 0 inches through about 0.012 inches.

8. The catheter device of claim 1, wherein the polymeric potting material comprises an elastomer.

9. The catheter device of claim 1, wherein the polymeric potting material comprises a cast elastomer.

10. The catheter device of claim 1, wherein the polymeric potting material comprises a cast polyurethane.

11. The catheter device of claim 10, wherein the cast polyurethane comprises a thermoset polyurethane adhesive.

12. The catheter device of claim 1, wherein the inner liner comprises a tube having a thickness ranging from about 0.00025 inches through about 0.002 inches.

13. The catheter device of claim 1, wherein the inner liner comprises at least one material selected from the group consisting of: fluoropolymers; PTFE; PFA; and FEP.

14. The catheter device of claim 1, wherein the inner liner comprises PTFE having a thickness of about 0.0005 inch.

15. The catheter device of claim 1, wherein the outer cover has a thickness ranging from about 0.0005 inch through about 0.002 inch.

16. The catheter device of claim 1, wherein the outer cover comprises at least one material selected from the group consisting of polyesters and polyolefins.

17. The catheter device of claim 1, wherein the outer cover comprises polyester and or polyolefin having a thickness of about 0.0005 inch.

18. The catheter device of claim 1, wherein the catheter device has a plurality of regions along its length, wherein dimension(s) of the metal helix and/or the width of the helical gap differ between the plurality of regions.

19. The catheter device of claim 18, wherein the catheter device has a proximal region, and a distal region.

20. The catheter device of claim 19, wherein the helical member in the proximal region has a width of about 0.008 inch, a thickness of about 0.0025 inch and a helical gap of about 0 to 0.004 inches and the helical member in the distal region has a width of about 0.008 inch, a thickness of about 0.002 inch and a helical gap of about 0.002 to 0.012 inches.

21. The catheter device of claim 20, wherein the outer cover on the proximal region comprises polyester having a thickness of about 0.001 inch and the outer over on the distal region comprises polyolefin or polyamide copolymer having a thickness of about 0.0005 to 0.001 inch.

22. The catheter device of claim 21, wherein the distal region has a lateral flexibility of greater than 1200 degree/in-lb.

23. The catheter device of claim 21, wherein the distal region has a kink radius of about 0.174 inch +/−0.008 inch or less.

24. The catheter device of claim 21, wherein the distal region has a wall thickness to inner diameter ratio in excess of 16:1.

25. The catheter device of claim 21, wherein the distal region has an ultimate tensile strength of greater than 15N's.

26. The catheter device of claim 1, wherein the catheter device has a proximal region, a medial region, and a distal region.

27. The catheter device of claim 26, wherein the helical member in the proximal region has a width of about 0.008 inch, a thickness of about 0.0025 inch and a helical gap of about 0 to 0.002 inches; the helical member in the medial region has a width of about 0.008 inch, a thickness of about 0.002 inch and a helical gap of about 0.002 to 0.006 inches, and the helical member in the distal region has a width of about 0.004 inch, a thickness of about 0.002 inches and a helical gap of about 0.002 to 0.012 inches.

28. The catheter device of claim 27, wherein the outer cover on the proximal region comprises polyester having a thickness of about 0.001 inch; the outer cover on the medial region comprises polyester having a thickness of about 0.0005 to 0.001 inch and the outer cover on the first and second distal regions comprises polyolefin or Nylon copolymer having a thickness of about 0.0005 inch.

29. The catheter device of claim 28, wherein the distal region has a lateral flexibility of greater than 1,200 degree/in-lb.

30. The catheter device of claim 28, wherein the distal region has a kink radius of about 0.174 inch +/−0.008 inch or less.

31. The catheter device of claim 28, wherein the distal region has a wall thickness to inner diameter ratio in excess of 16:1.

32. The catheter device of claim 28, wherein the distal region has an ultimate tensile strength of greater than 15N's.

33. The catheter device of claim 1 further comprising a balloon.

34. The catheter device of claim 33, wherein the balloon comprises a compliant balloon.

35. The catheter device of claim 33, wherein the balloon comprises a substantially non-compliant membrane.

36. The catheter device of claim 1, wherein the polymer disposed within the helical gap is a thermoset polymer.

37. The catheter device of claim 1, wherein the balloon inflation channel walls comprise polyimide.

38. The catheter device of claim 33, wherein a lumen of the balloon inflation channel terminates under, and is operably connected to, the balloon, the balloon being fluidically sealed to the catheter tubing proximal, and distal, to the termination of the balloon inflation channel.

39. The catheter device of claim 1, further comprising a proximal region and a distal region having different flexibility, wherein the metal helix in the distal region comprises a different cross-section than the metal helix in the proximal region.

40. The catheter device of claim 1, further comprising a proximal region and a distal region having different flexibility, wherein the metal helix in the distal region comprises a different a cross-section that is thinner than the cross-section of the metal helix in the proximal region.

41. The catheter device of claim 1, further comprising a proximal region and a distal region having different flexibility, wherein the metal helix in the distal region comprises a pitch that is looser than the pitch of the metal helix in the proximal region.

42. The catheter device of claim 1, further comprising a proximal region and a distal region having different flexibility, wherein the metal helix in the distal region is more tightly wound around the inner liner than the metal helix in the proximal region.

43. The catheter device of claim 1 further comprising a relatively stiff proximal tubing segment, a relatively flexible distal tubing segment, and at least one intermediate segment defining a passageway between the relatively stiff proximal tubing segment and the relatively flexible distal tubing segment.

44. The catheter device of claim 43 further comprising a transition region between the proximal segment and the intermediate segment.

45. The catheter device of claim 43 further comprising a transition region between the intermediate segment and the distal segment.

46. A method for treating or diagnosing a disorder in a human or animal subject, the method comprising:

inserting into the subject's vasculature a catheter device comprising:
an axially elongate tubular member comprising an inner lumen, an outer surface, a proximal end, and a distal end, the tubular member comprising a metal helix having a helical gap, and a polymeric potting material disposed within the helical gap;
an inner liner extending through the lumen of the tubular member and defining an inner lumen of the catheter;
an outer covering on the outer surface of the tubular member; and
a balloon inflation channel sandwiched between the metal helix and the inner liner, wherein the balloon inflation channel comprises a separate polymeric tubular structure,
wherein the polymeric potting material disposed within the helical gap is different from the materials of the inner liner and outer cover;
inflating a balloon affixed to the catheter device proximate to the distal end of the catheter device, the balloon being inflated from a first, uninflated configuration to a second, inflated configuration;
delivering a substance or device through the lumen of the catheter device to treat or diagnose the disorder;
deflating the balloon to a third, uninflated configuration; and
removing the catheter device from the human or animal subject.

47. The method of claim 46, further comprising advancing the catheter device into a blood vessel located within the subject's skull.

48. The method of claim 47, wherein the blood vessel into which the catheter device is advanced is selected from the group consisting of: carotid artery, cerebral artery, anterior cerebral artery, middle cerebral artery and posterior cerebral artery.

49. The method of claim 46, further comprising occluding blood flow within a vessel or lumen.

50. The method of claim 46, further comprising aspirating fluid from a blood vessel or lumen.

51. The method of claim 46, further comprising aspirating fluid from a blood vessel or lumen substantially during retrieval or delivery of a device, embolic material, or fluid into the blood vessel or lumen.

52. The method of claim 46, further comprising pulling or withdrawing a material or substance into the lumen of the catheter while the balloon is in its second, inflated configuration.

* * * * *